United States Patent
Hsieh et al.

(10) Patent No.: US 11,065,398 B2
(45) Date of Patent: Jul. 20, 2021

(54) AEROSOL GENERATING APPARATUS

(71) Applicant: MICROBASE TECHNOLOGY CORP., Taoyuan (TW)

(72) Inventors: Shu-Pin Hsieh, Taoyuan (TW);
Yi-Tong Chen, Taoyuan (TW);
Po-Chuan Chen, Taoyuan (TW);
Ting-Kai Tsai, Taoyuan (TW);
Chih-Wei Lu, Taoyuan (TW);
Laurence Kao, Taipei (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 0 days.

(21) Appl. No.: 16/097,272

(22) PCT Filed: Jul. 19, 2017

(86) PCT No.: PCT/US2017/042687
§ 371 (c)(1),
(2) Date: Oct. 28, 2018

(87) PCT Pub. No.: WO2018/017627
PCT Pub. Date: Jan. 25, 2018

(65) Prior Publication Data
US 2019/0117908 A1    Apr. 25, 2019

Related U.S. Application Data

(60) Provisional application No. 62/364,309, filed on Jul. 19, 2016.

(51) Int. Cl.
*A61M 11/00* (2006.01)
*B05B 15/18* (2018.01)
(Continued)

(52) U.S. Cl.
CPC ...... *A61M 11/005* (2013.01); *A61M 15/0001* (2014.02); *A61M 15/0085* (2013.01);
(Continued)

(58) Field of Classification Search
CPC ............ A61M 11/005; A61M 11/0001; A61M 15/0085; A61M 2205/123;
(Continued)

(56) References Cited

U.S. PATENT DOCUMENTS 6,446,880 B1 * 9/2002 Schram ............... B05B 17/0646
222/570
2005/0011514 A1  1/2005 Power et al.
(Continued)

FOREIGN PATENT DOCUMENTS

EP         2957349 A1   12/2015
WO   WO2011/083380 A1   7/2011

OTHER PUBLICATIONS

Extended European Search Report for application No. 17831732.7, dated Apr. 1, 2019.
(Continued)

*Primary Examiner* — Margaret M Luarca
(74) *Attorney, Agent, or Firm* — Polsinelli PC

(57) ABSTRACT

An aerosol generating apparatus is disclosed. The apparatus includes a liquid container, an adaptor and a driving element. The liquid container includes a perforated membrane through which a liquid can permeate. The liquid container further includes a first mating element. The adaptor includes a second mating element. The driving element includes a piezoelectric element coupled to a substrate. The driving element is accommodated by the adaptor and the substrate includes an aperture and a projection. The first and second mating elements are adapted to detachably and slidably mate with each other such that the aperture of the substrate aligns (Continued)

proximately to the center of the perforated membrane. The first and second mating elements are further adapted for relative movement along a sliding axis. The projection is adapted to press against the perforated membrane.

19 Claims, 16 Drawing Sheets

(51) Int. Cl.
  *B05B 17/06* (2006.01)
  *A61M 15/00* (2006.01)
  *B05B 17/00* (2006.01)
(52) U.S. Cl.
  CPC .......... *B05B 15/18* (2018.02); *B05B 17/0646* (2013.01); *B05B 17/0653* (2013.01); *A61M 2205/0294* (2013.01); *A61M 2205/121* (2013.01); *A61M 2205/123* (2013.01)
(58) Field of Classification Search
  CPC ......... A61M 2205/121; B05B 17/0653; B05B 17/0646; B05B 17/06; B05B 17/0607; B05B 17/0638
  See application file for complete search history.

(56) References Cited

U.S. PATENT DOCUMENTS

| | | | |
|---|---|---|---|
| 2006/0102172 | A1 | 5/2006 | Feiner et al. |
| 2008/0308096 | A1* | 12/2008 | Borgschulte ...... A61M 15/0085 128/200.14 |
| 2011/0011394 | A1* | 1/2011 | Edwards ................ A23G 1/305 128/200.18 |
| 2011/0284656 | A1 | 11/2011 | Kamrayashi et al. |
| 2012/0291776 | A1* | 11/2012 | Van Der Mark .... A61M 11/005 128/200.14 |
| 2013/0119151 | A1 | 5/2013 | Moran et al. |
| 2013/0126637 | A1* | 5/2013 | Hsieh ................... A61M 11/005 239/102.2 |
| 2014/0110499 | A1 | 4/2014 | Fang et al. |
| 2016/0158789 | A1 | 6/2016 | Selby et al. |
| 2018/0178240 | A1* | 6/2018 | Anzenberger ....... A61M 11/005 |

OTHER PUBLICATIONS

Blaine R Copenheaver, The internationl search report and the written opinion of the Internaional Search Authority, dated Oct. 3, 2017, whole codument, USPTO as ISA.

* cited by examiner

AEROSOL GENERATING APPARATUS

CROSS REFERENCE TO RELATED APPLICATION

The present application claims priority to PCT Application PCT/US2017/042687 filed on Jul. 19, 2017, which claims priority to U.S. Provisional Application Ser. No. 62/364,309 filed on Jul. 19, 2016, the entire contents of which are hereby incorporated by reference into this application.

FIELD

The present disclosure relates to an aerosol generating apparatus and more particularly to an aerosol generating apparatus with interchangeable components that have novel engagement mechanisms which allow them to properly align.

BACKGROUND

Nebulizers, also known as aerosolizer or atomizer, are used to deliver medication in fine particles/droplets to patients for inhalation. An aerosol generating module, which is a component of a nebulizer, receives liquid medicament to generate aerosol for treating a patient with respiratory conditions, such as Chronic Obstructive Pulmonary Disease (COPD). A typical aerosol generating module includes a perforated membrane and a vibratable element. One way for a vibratable element to generate vibration is through the incorporation of piezoelectric (PZT) materials. Vibration is provided to the liquid passing through the perforated membrane, thereby generating aerosolization.

A reservoir or a liquid container, with an internal chamber, stores the liquid medicament to be provided to the aerosol generating module. The vibratable element vibrates the perforated membrane, through which the liquid medicament permeates, to generate aerosolization. Typically, the aerosol generating module is either permanently secured to the liquid container or integrally formed with the liquid container. The aerosol generating module may be secured to the liquid container with adhesives or by other known securing means. Accordingly, when the liquid medicament is depleted, the aerosol generating module, which is permanently affixed to the liquid container, is also discarded.

Generally, the liquid container needs to be cleaned thoroughly prior to each use. The same applies to the perforated membrane. If the liquid container and/or the perforated membrane were not cleaned properly, the nebulizer may not work in subsequent use. For example, residue may form and block the perforated membrane. The vibratable element, if not cleaned adequately, may degrade fast and generate liability and performance issues. The liquid medicament may also be contaminated due to insufficient cleaning. The abovementioned risks can be mitigated by using a new set of aerosol generating module and liquid container for every treatment. However, it will substantially increase the patient's financial burden.

Therefore, the present disclosure aims to design a nebulizer with interchangeable and replaceable components such as liquid container, perforated membrane and vibratable element. The present disclosure also aims to provide means for precisely aligning the liquid container, the perforated membrane, and the vibratable element. The present disclosure further aims to disclose novel means of mating and engaging the liquid container with an adaptor accommodating the perforated membrane and the vibratable element. The present disclosure yields higher nebulization quality and efficiency while providing patient with a cost-effective treatment solution.

SUMMARY

The disclosure provides an aerosol generating apparatus having a liquid container, an adaptor and a driving element. The liquid container includes a perforated membrane through which a liquid can permeate, the liquid container further includes a first mating element. The adaptor includes a second mating element. The driving element includes a piezoelectric element coupled to a substrate. The driving element is accommodated by the adaptor and the substrate includes an aperture and a projection. The first and second mating elements are adapted to detachably and slidably mate with each other such that the aperture of the substrate aligns proximately to the center of the perforated membrane. The first and second mating elements are further adapted for relative movement along a sliding axis. The projection is adapted to press against the perforated membrane.

In some embodiments, the first and second mating elements are adapted to move along a sliding axis until a full mate condition is reached.

In some embodiments, the first mating element includes a groove which engages a mating tongue on the second mating element.

In some embodiments, the first mating element includes a tongue which engages a mating groove on the second mating element.

In some embodiments, the adaptor further comprises at least one jack for contacting and supporting the substrate.

In some embodiments, the liquid container includes a third mating element adapted to annularly surround the liquid container. The adaptor includes a fourth mating element in the shape of a circular surface and adapted to located at the top edge of the adaptor. The third and fourth mating elements adapted to mate and engage with each other such that the relative position of the liquid container and the adaptor maintains station.

In some embodiments, the extent in which the perforated membrane is being pressed by the projection is predetermined by the positions of the first and second mating elements.

In some embodiments, the first mating element includes a helical thread surface which rotatably engages a mating helical thread surface on the second mating element.

The disclosure further provides an aerosol generating apparatus having a liquid container, an adaptor and a driving element. The liquid container includes a perforated membrane through which a liquid can permeate. The liquid container further includes a first mating element. The adaptor includes a second mating element. The driving element includes a piezoelectric element coupled to a substrate. The driving element is accommodated by the adaptor and the substrate includes an aperture and a projection. The first and second mating elements are adapted to detachably mate with each other such that the aperture of the substrate aligns proximately to the center of the perforated membrane. The projection is adapted to press against the perforated membrane when the first and second mating elements are engaged.

In some embodiments, the first and second mating elements are adapted to engage with each other using a connection selecting from the group consisting of a snap-fit, an interference fit, a tongue-and-groove fit, a post-and-bore fit, and a press-fit.

In some embodiments, the first mating element is further adapted to move in a longitudinal direction.

In some embodiments, the extent in which the perforated membrane is being pressed by the projection correlates to a relative movement of the first mating element in the longitudinal direction.

In some embodiments, the adaptor further comprises at least one jack for contacting and supporting the substrate.

In some embodiments, the first mating element includes a protruding part and the second mating element includes a cavity. The protruding part is adapted to deflect briefly during mating and then catches in the cavity. The protruding part is selected from a group consisting of a hook, a stud or a bead. The protruding part may extend annually or semi-annually around the liquid container, while the mating cavity may also extend annually or semi-annually inside the adaptor.

In some embodiments, the first mating element further includes a first contacting surface. The second mating element further includes a second contacting surface. The first and second contact surfaces are adapted to create friction such that the liquid container and adaptor are securely engaged.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

Figure 1:
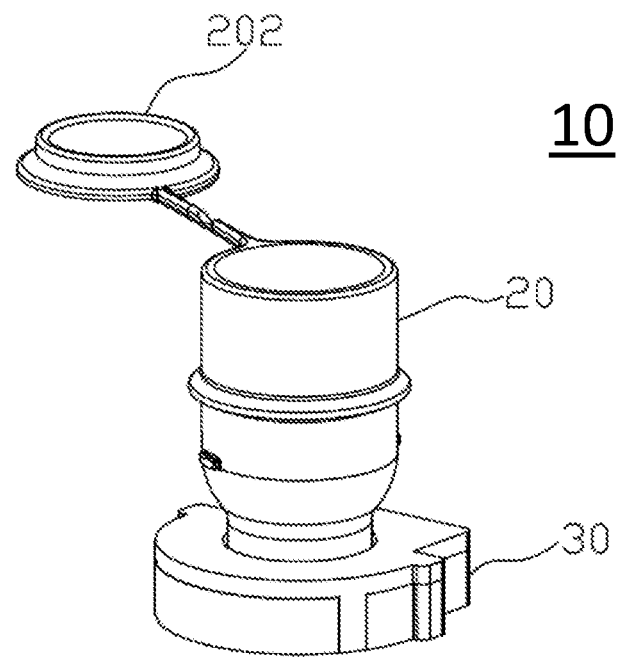
FIGS. 1-2 are side views of an aerosol generating apparatus in accordance with some embodiments of the present disclosure.

The drawings are only schematic and are non-limiting. In the drawings, the size of some of the elements may be exaggerated and not drawn on scale for illustrative purposes. The dimensions and the relative dimensions do not necessarily correspond to actual reductions to practice of the invention. Any reference signs in the claims shall not be construed as limiting the scope. Like reference symbols in the various drawings indicate like elements.

DETAILED DESCRIPTION OF THE DISCLOSURE

The making and using of the embodiments of the disclosure are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Throughout the various views and illustrative embodiments, like reference numerals are used to designate like elements. Reference will now be made in detail to exemplary embodiments illustrated in the accompanying drawings. Wherever possible, the same reference numbers are used in the drawings and the description to refer to the same or like parts. In the drawings, the shape and thickness may be exaggerated for clarity and convenience. This description will be directed in particular to elements forming part of, or cooperating more directly with, an apparatus in accordance with the present disclosure. It is to be understood that elements not specifically shown or described may take various forms. Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. It should be appreciated that the following figures are not drawn to scale; rather, these figures are merely intended for illustration.

In the drawings, like reference numbers are used to designate like or similar elements throughout the various views, and illustrative embodiments of the present disclosure are shown and described. The figures are not necessarily drawn to scale, and in some instances the drawings have been exaggerated and/or simplified in places for illustrative purposes. One of ordinary skill in the art will appreciate the many possible applications and variations of the present disclosure based on the following illustrative embodiments of the present disclosure.

It will be understood that when an element is referred to as being "on" another element, it can be directly on the other element or intervening elements may be present. In contrast, when an element is referred to as being "directly on" another element, there are no intervening elements present.

It will be understood that singular forms "a", "an" and "the" are intended to include the plural forms as well, unless the context clearly indicates otherwise. Furthermore, relative terms, such as "bottom" and "top," may be used herein to describe one element's relationship to other elements as illustrated in the Figures.

It will be understood that elements described as "under" or "below" other elements would then be oriented "over" or "above" the other elements. The exemplary terms "under" or "below" can, therefore, encompass both an orientation of over and under.

Unless otherwise defined, all terms (including technical and scientific terms) used herein have the same meaning as commonly understood by one of ordinary skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
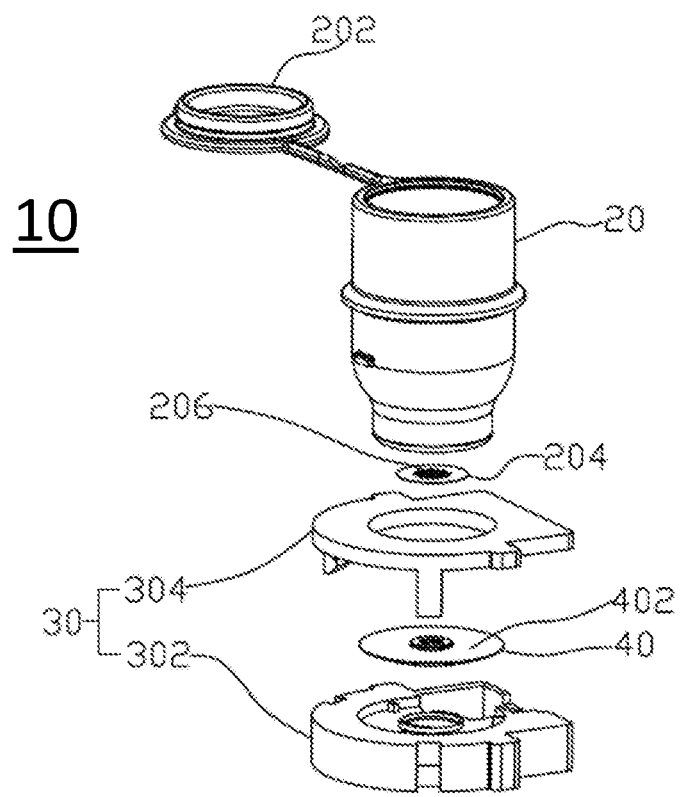

FIGS. 1-2 are side views of an aerosol generating apparatus in accordance with some embodiments of the present disclosure.

Referring to FIG. 1, an aerosol generating apparatus 10 is disclosed. The aerosol generating apparatus 10 includes a liquid container 20 and a corresponding adaptor 30. Here, the liquid container 20 is engaged with the adaptor 30. As will be discussed in subsequent disclosures and embodiments, the liquid container 20 and the adaptor 30 can be disengaged. As such, users are allowed to replace the liquid container 20 while continue to use the same adaptor 30. Conversely, users may replace the adaptor 30 and/or the components therein when it is damaged or after prolonged use, while continue to use the same liquid container 20.

The liquid container 20 is configured to hold a liquid medicament (not shown) or any medication suitable for aerosolization to be provided to the aerosol generating apparatus 10. The liquid container 20 may include a lid 202 covering an inlet, through which users can re-fill the liquid medicament. Alternatively, the liquid container 20 may not include such lid 202. Accordingly, users need to replace the liquid container entirely when the liquid medicament is depleted. The liquid container 20 includes an outlet opening (not shown) facing the adaptor 30. Through such opening, liquid is provided to the adaptor 30 for aerosolization.

The adaptor 30 is configured to house aerosolization components therein, which will be discussed in subsequent disclosures and embodiments. The adaptor 30 includes an inlet at one side for receiving liquid from the liquid container 20 and an outlet opposite to the inlet. Liquid enters the adaptor 30 and exits through the outlet in the form of aerosol. As such, the adaptor 30 is made of impermeable material(s). Moreover, the adaptor 30 may accommodate electric wires (not shown) for delivery of electric power to certain components therein. The impermeable material also serves to improve the durability of such electric parts.

Aerosolization is to be conducted after the liquid container 20 and the adaptor 30 is engaged. The relative position between the liquid container 20 and the adaptor 30 is fixed during aerosolization to ensure the liquid medicament is aerosolized under a controlled manner. Still, their relative position may be adjusted to configure the aerosolization rate based on different needs.

FIG. 2 illustrates the aerosol generating apparatus 10 with the liquid container 20 disengaged from the adaptor 30. Further, relevant components accommodated by the liquid container 20 and the adaptor 30 are shown in an exploded view. Here, the liquid container 20 includes a membrane 204 at its outlet opening. At least part of the membrane 204 is porous. That is, the membrane 204 includes a plurality of orifices 206 for the liquid medicament to eject. Therefore, the membrane 204 may also be referred to as a perforated membrane. Exemplary ways of forming the orifices 206 include etching or laser drilling. The orifices 206 can also be formed by other method known to persons having ordinary skill in the art. The size of the orifices 206 is configured to substantially prevent liquid medicament from leaking. In certain embodiments, the orifices 206 are positioned around the center of the membrane 204. In some embodiments, the orifices 206 may be distributed all over the membrane 204 or at certain sections only, depending on the configuration of the rest of the components of the aerosol generating apparatus 10.

In some embodiments, the membrane 204 is made of a material flexible enough to respond to vibration, yet sturdy enough to maintain liquid from leakage or prevent contamination from outside environment. In certain embodiments, the membrane 204 is made of a macromolecular polymer of polyimide, polyethylene (PE), polypropylene (PP), polyether ether ketone (PEEK) and/or the combination thereof. When the membrane 204 is integrally formed with the liquid container 20, the two are made of the same material or same combination of materials. A separate container or vial may be added to encase the liquid container 20.

The adaptor 30 may include a body 302 and an interface 304. Together they may form a chamber for accommodating components therein. The body 302 and the interface 304 may be integrated into one single structure. Alternatively, only the body 302 is needed to accommodate elements therein and for engaging with the liquid container 20. In certain embodiments, the interface 304 may serve to mate, align and/or affix the liquid container 20 to the adaptor 30. For example, the liquid container 20 and the interface 304 may be joined by a tongue-groove or a snap-fit connection. A person having ordinary skill in the art would understand that other mating/aligning/affixing mechanisms may applied as long as the relative position between the liquid container 20 and the adaptor 30 can be maintained during aerosolization. If such positions are not maintained, the liquid container 20 may shift or jolt during aerosolization. As a result, aerosolization efficiency will be affected. Moreover, components of the aerosol generating apparatus 10 may be more prone to damage and wear if the position of the liquid container 20 and the adaptor 30 is not maintained.

A driving element 40 is accommodated by the adaptor 30. The driving element includes a piezoelectric (PZT) element (404, not shown) and a substrate 402. The substrate 402 may be flat or with a projection. The substrate 402 is made of metal or any kind of material suitable for prolonged vibration without breakage. The PZT element 404 is coupled to the liquid outlet side of the substrate 402, and the liquid inlet side of the substrate 402 faces the membrane 204. When the liquid container 20 is engaged with the adaptor 30, the substrate 402 and the membrane 204 are in contact. During aerosolization, electric power is provided to the PZT element through electric contacts, such as wires or leads. As a result, the PZT element 404 vibrates and the vibration energy thereof is transmitted to the membrane 204 to aerosolize the liquid passing through. The liquid container 20 and the adaptor 30 may respectively include some additional structures/components to ensure that the positioning of the liquid container 20, the membrane 204 and the adaptor 30 are in a desired manner, e.g., aligned. Such additional structures/components will be discussed in the subsequent disclosure.

Figure 3:
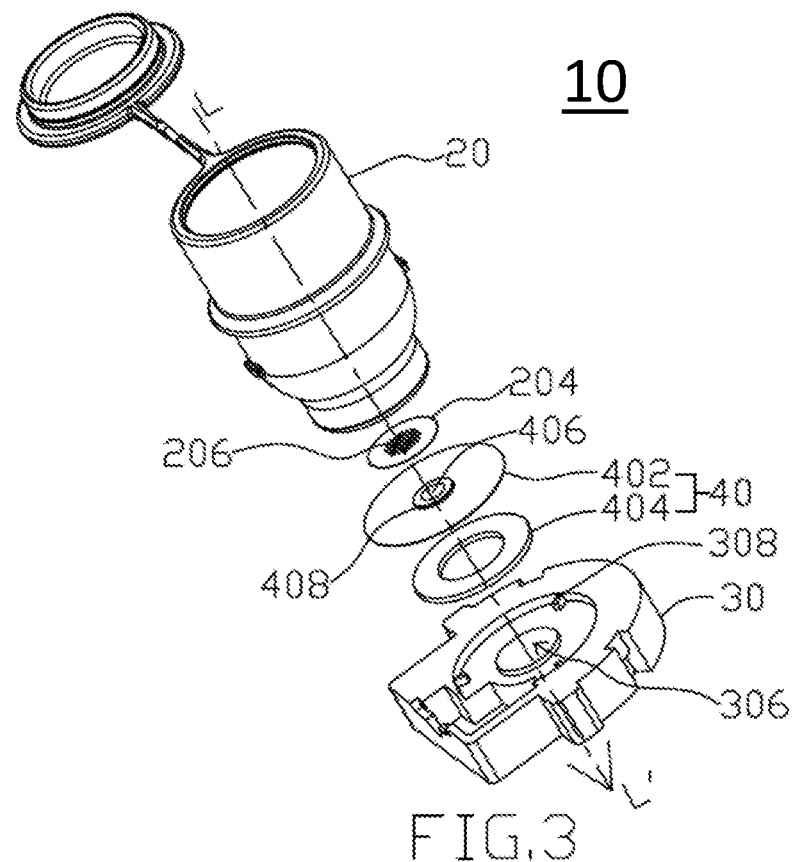
FIG. 3 illustrates an exploded view of an aerosol generating apparatus 10 according to some embodiments of the present disclosure.

FIG. 3 illustrates an exploded view of an aerosol generating apparatus 10 according to some embodiments of the present disclosure. Liquid medicament travels from the liquid container 20 towards the adaptor 30 along the dotted line L-L'. The PZT element 404 is positioned at the liquid outlet side of the substrate 402. Alternatively, although not shown here, the PZT element 404 may be positioned at the liquid inlet side of the substrate 402 and face the liquid container 20. A distance/spacing between the PZT element 404 and the adaptor 30 is always maintained such that the vibration of the PZT element 404 will not be hindered by the adaptor 30.

In certain embodiments, the substrate 402 includes an aperture 406 at about its center. The aperture 406 corresponds to the location of the orifices 206 of the membrane 204 when the liquid container 20 is engaged with the adaptor 30. As such, liquid can be directed from the liquid container 20 through the substrate 402 via such aperture 406. Aerosolized liquid then leaves the substrate 402 through such aperture 406 and exits the adaptor 30 via its through hole 306.

In certain embodiments, the substrate 402 includes a projection 408 corresponding to the location of the aperture 406. In other words, substrate 402 is elevated at the projection 408, which becomes in contact with the membrane 204 when the liquid container 20 and the adaptor 30 are engaged. In some embodiments, only the projection 408 is in contact with the membrane 204 during aerosolization. The projection 408 may also serve to partially deform the membrane 204 when the liquid container 20 and the adaptor 30 are engaged. One example is when the substrate 402/projection 408 presses against the liquid container 20/membrane 204. Aerosolization effect may be adjusted accordingly.

When the liquid container 20 and the adaptor 30 are engaged, the adaptor 30 is configured to contact the substrate's 40 periphery. The periphery of the substrate 40 shall be the outer perimeter of the substrate 40. In other words, it is the border area of the substrate 40 as distinguished from its internal regions or center. An example of the periphery of the substrate 40 is the ring region that marks the outer most boundary of the substrate 40. The adaptor 30 is configured to be in contact with the periphery of the substrate 402 for the purpose of minimizing hindrance against the vibration of the substrate 402 and for improving aerosolization efficiency. More particularly, the adaptor 30 is configured to make contact with only part of the periphery of the substrate 40.

Any contact of the substrate 402 with any element will create a hindered and/or dead spot during vibration, thus affecting vibration efficiency. It is preferred that the substrate 402 receives as little hindrance as possible. Moreover, hindrance from the periphery region of the substrates creates less energy loss than that from the more central regions. In the present disclosure, a jack 308 is provided at the adaptor 30 to achieve the foregoing goal. That is, the jack 308 of the adaptor 30 makes contact with the substrate 402 only at a specific location of its periphery. Accordingly, there is only minimal contact between the adaptor 30 and the substrate 402. The jack 308 may be attached to the adaptor 30 or integrally formed with the adaptor 30.

The jack 308 further serves to ensure that the substrate 402 will be placed at a predetermined position for desired aerosolization. For example, the jack 308 may serve to align the adaptor 30 and the substrate 402. The resulting aerosol generating apparatus 10 may deliver more desired aerosolization with less energy consumption. Higher aerosolization efficiency may also lead to fewer blockages or clogging, thus prolongs the life of the aerosol generating apparatus 10. In some embodiments, the jack 308 is made of materials other than metal, such as polymer.

In certain embodiments, the adaptor 30 includes only one jack 308. The periphery of the substrate 402 may be mounted on and supported by such one jack 308 without adhesive. However, in the one jack 308 configuration, it is recommended that adhesive, e.g., glue, gel, hot molding or welding, is applied in order to maintain structural strength and integrity. Alternatively, the adaptor 30 may include more than one, e.g., two, three or more, jacks 308, that also correspond to the substrate's 402 periphery. Here, adhesive is optional between the plurality of jacks 308 and the substrate 402.

When engaged, the substrate 402 only makes contact with the tips of the plurality of jacks 308 at the periphery. Accordingly, only small areas of the periphery where the jacks 308 touch the substrate 402 may be affected during vibration. In other words, the adaptor 30 supports the substrate 402 just enough to maintain position during vibration/aerosolization, allowing substrate 402 to vibrate freely with minimal hindrance. In certain embodiments, this may be considered as the substrate 402 is partially supported by the adaptor 30. Such minimal hindrance provides an aerosol generating apparatus capable of delivering desired aerosolization with reduced energy consumption. It is important to note that the foregoing disclosure is only exemplary and shall not be considered as exhaustive. A person having ordinary skill in the art will understand that the configuration of any number of jacks 308 will fall within the scope of the present disclosure as long as the contact between the substrate 402 and the adaptor 30 is minimal. In a preferred embodiment, the adaptor 30 is only in contact with the periphery of the substrate 402 at no more than three locations, in the form of tip of a jack or any other readily known supporting structure.

The jack 308 further serves to lift and maintain the substrate 402 at a certain height, i.e., away from the liquid inlet surface of the adaptor 30. In other words, a space is maintained between the liquid inlet surface of the adaptor 30 and the substrate 402. Without such space, additional sections of the substrate 402 may come in contact with the adaptor 30 when vibrated, which results in vibration hindrance and loss. Moreover, such space serves to accommodate the PZT element 404 that couples to the substrate 402. The PZT element 404 is disposed at the liquid outlet surface of the substrate 402. Some space between the substrate 402 and the adaptor 30 should be preserved to prevent the PZT element 404 from contacting the adaptor 30. With such space maintained, vibration energy will not be reduced and vibration pattern of the substrate 402 will not be hindered.

Figure 4:
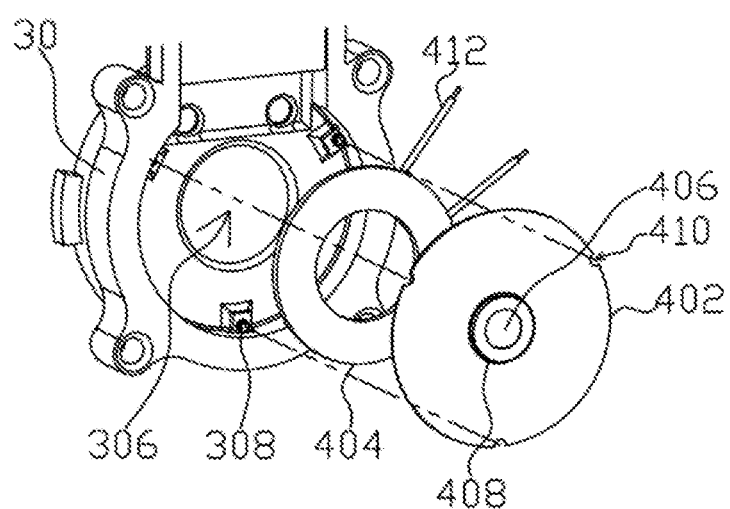
FIG. 4 is an exploded view of part of the aerosol generating device according to some embodiments of the present disclosure.

FIG. 4 is an exploded view of part of the aerosol generating device according to some embodiments of the present disclosure. In order to be better supported by the jacks 308, the substrate 402 may include a mating structure 410 that corresponds to the jack 308. For example, the mating structure 410 may be an indention or recess corresponding to the shape of the jack 308. As a result, when engaged along the dotted lines, the substrate 402 is directed to a predetermined position where the mating structure 410 and the jack 308 match. Correspondingly, the aperture 406 may be directed to another predetermined position suitable for better aerosolization. Moreover, the substrate 402 may become fitted with the jack 308 such that horizontal movement during aerosolization is reduced or inhibited. In another example, the aperture 406 is then aligned with the through hole 306 of the adaptor 30 such that aerosolized liquid can leave the adaptor 30 without obstruction. Again, there may be any numbers (one, two, three or more) of jack(s) 308 at the adaptor 30, and therefore there may be corresponding numbers of mating structure 410 at the substrate 402.

Here, the electric contact 412 of the PZT element 404 is illustrated. Such electric contact 412 may be leads or electric wires. It is configured to provide electric power to the PZT element 404 to create vibration. Such vibration is then transmitted to the membrane 204 through the substrate 402 for aerosolization. In general, the PZT element 404 is ring shaped so aerosolized liquid can pass through its central through hole. However, the shape of the PZT element 404 is not limited to circular and may be adjusted if needed. For example, the shape of the PZT element 404 may not be a complete ring. It can be C-shaped or an incomplete ring with gaps. As long as vibration energy can be transmitted from the periphery towards the center of the substrate 402, the PZT element 404 can be of any shape or form.

Figure 5:
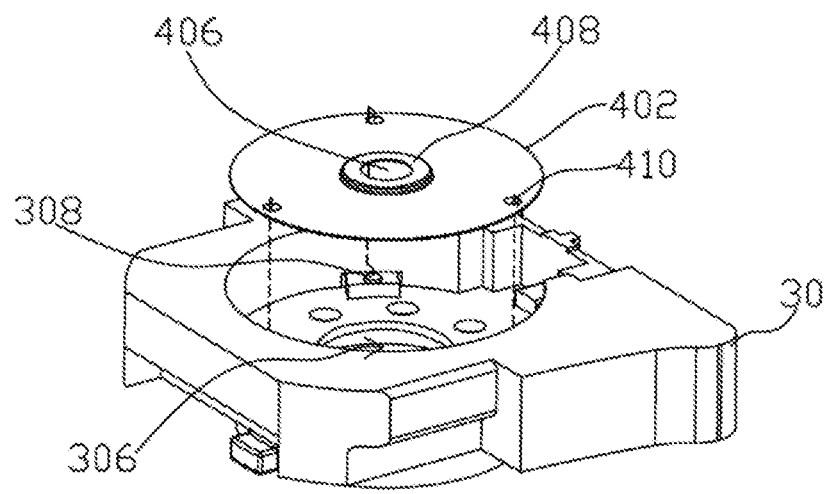
FIGS. 5-7 are side views of part of an aerosol generating apparatus according to some embodiments of the present disclosure.
Figure 6:
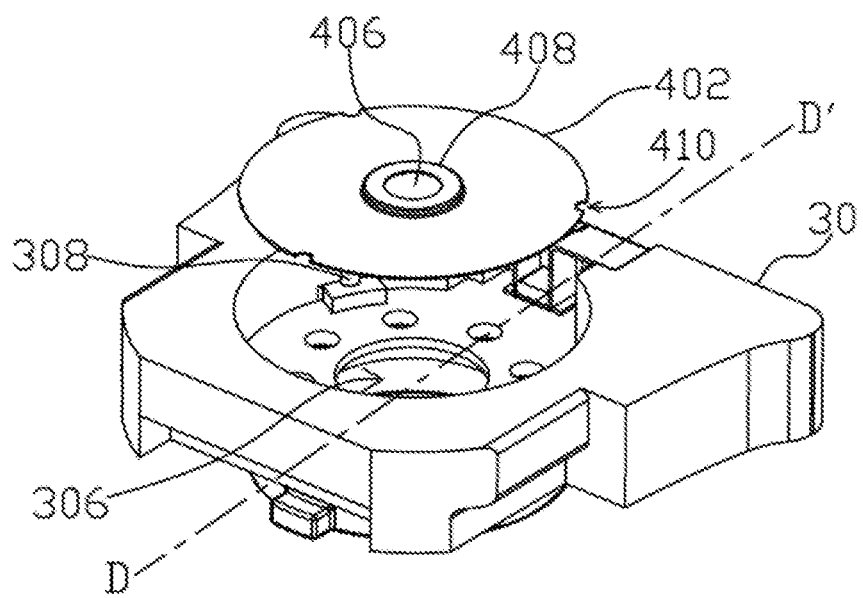
Figure 7:
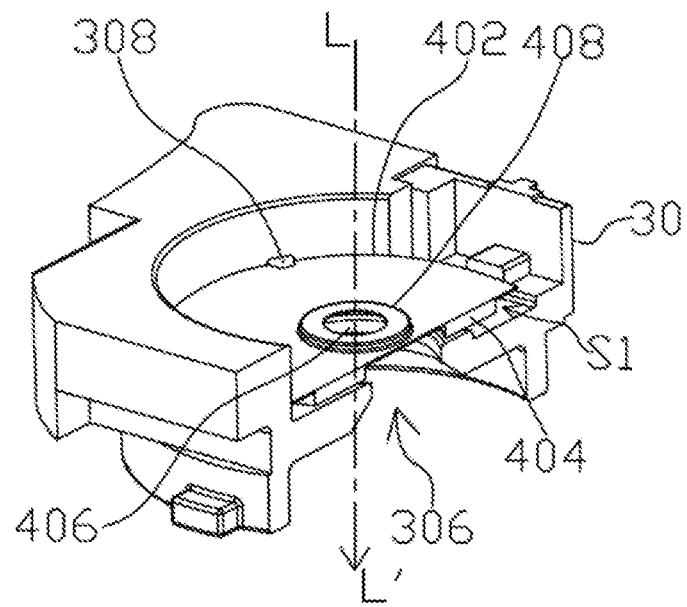

FIGS. 5-7 are side views of part of an aerosol generating apparatus in accordance with some embodiments of the present disclosure.

In FIG. 5 shows the embodiment when the substrate 402 is not engaged with the adaptor 30. The aperture 406 is located substantially at the center of the substrate 402 and corresponds to the through hole 306 of the adaptor 30. As such, aerosolized liquid can exit the adaptor 30 without obstruction. The mating structure 410 is a puncture hole at the periphery of the substrate 402. Such mating structures 410 correspond to the jacks 308 of the adaptor 30. Accordingly, the substrate 402 is maintained at a predetermined position when the mating structure 410 is mated with the jack 308, i.e., when the substrate 402 is accommodated by the adaptor 30. In certain embodiments, the mating structure 410 may be a tab protruding out of the periphery of the substrate 402. In such embodiments, the corresponding supporting structure at the adaptor 30 would not be a jack or anything that protrudes out from the adaptor 30. Instead, it can be an indentation on the adaptor 30 to accommodate the protruding tab. It is to be noted that the number, structure, placement or configuration of the mating/supporting structure between the substrate 402 and the adaptor 30 should not be limited to only the embodiments disclosed herein. A person having ordinary skill in the art would understand that any mechanism that provides minimal contact between the substrate 402 and the adaptor 30 at the periphery of the substrate 402 should fall within the scope of this disclosure.

FIG. 6 shows another embodiment when the substrate 402 is not engaged with the adaptor 30. FIG. 7 shows the same embodiment when the substrate 402 is engaged with the adaptor 30. Particularly, FIG. 7 shows a cross-sectional view of the components along the dotted line D-D' in FIG. 6 but with the substrate 402 engaged with the adaptor 30. As illustrated, the substrate 402 is in contact with the adaptor 30 only at the jacks 308. In other words, except the jacks 308, the inner perimeter of the adaptor 30 surrounding the substrate 402 is not in contact with the substrate 402. Specifically, a space is formed and maintained between the substrate 402 and the adaptor 30 except where the jack 308 is. As such, there's limited or minimal hindrance against the vibration of the substrate 402 by the adaptor 30. The resulting driving element 40 generates desired vibration energy with less electric power consumption.

The liquid/aerosol flow direction from L to L' is again illustrated in FIG. 7. The substrate 402 includes a first liquid inlet side facing the liquid container (not shown), and a first liquid outlet side facing the adaptor 30. Furthermore, the adaptor 30 includes a second liquid inlet side facing the liquid container (not shown) and a second liquid outlet side at the through hole 306 where aerosolized liquid leaves the adaptor 30. As illustrated, a space S1 is maintained between the first liquid outlet side and the second liquid inlet side such that the two sides will not touch each other during aerosolization. The space S1 also serves to ensure that there is enough room between the first liquid outlet side and the second liquid inlet side to accommodate the PZT element 404. A preferred design is to ensure that PZT element 404 do not contact the adaptor 30. Otherwise, vibration of the PZT element 404 will be hindered and aerosolization efficiency will be affected. In certain embodiments, an O-ring (not shown), which seals the PZT element 404 from exposure to the outside environment, is disposed between the first liquid outlet side and the second liquid inlet side. The O-ring is essentially a cushion, and the aforementioned two sides may be considered as indirectly in contact with each other. Because the O-ring is made of at least one flexible material (s), the vibration of the PZT element 404 will not be hindered even with the O-ring in contact with both the first liquid outlet side and the second liquid inlet side. In other words, the space S1 may be occupied by the O-ring while the resulting aerosol generating apparatus 10 is still capable of delivering desired aerosolization efficiency.

Figure 8:
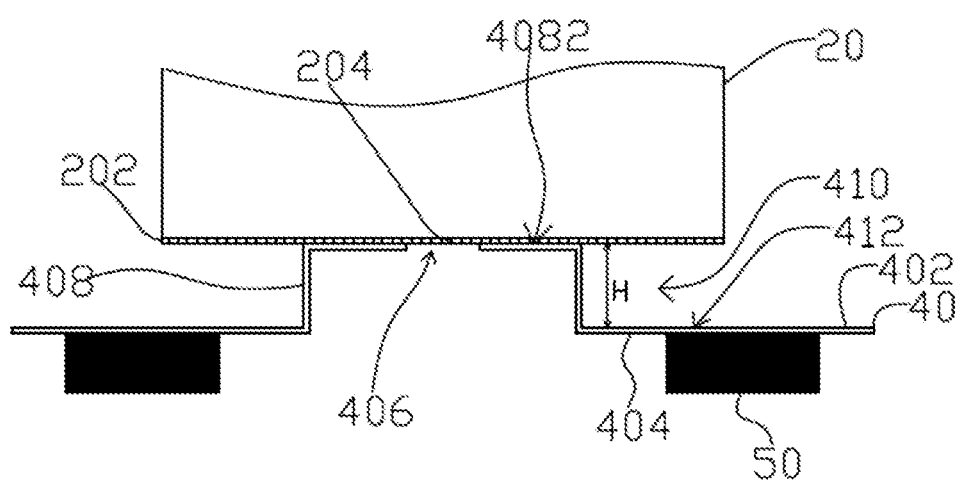
FIGS. 8-9 are partial views of an aerosol generating apparatus with interchangeable parts according to some embodiments of the present disclosure.
Figure 9:
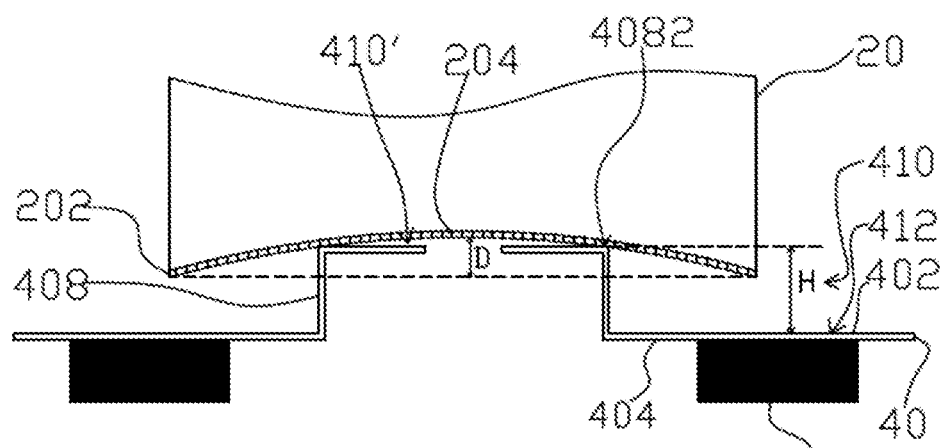
Figure 10:
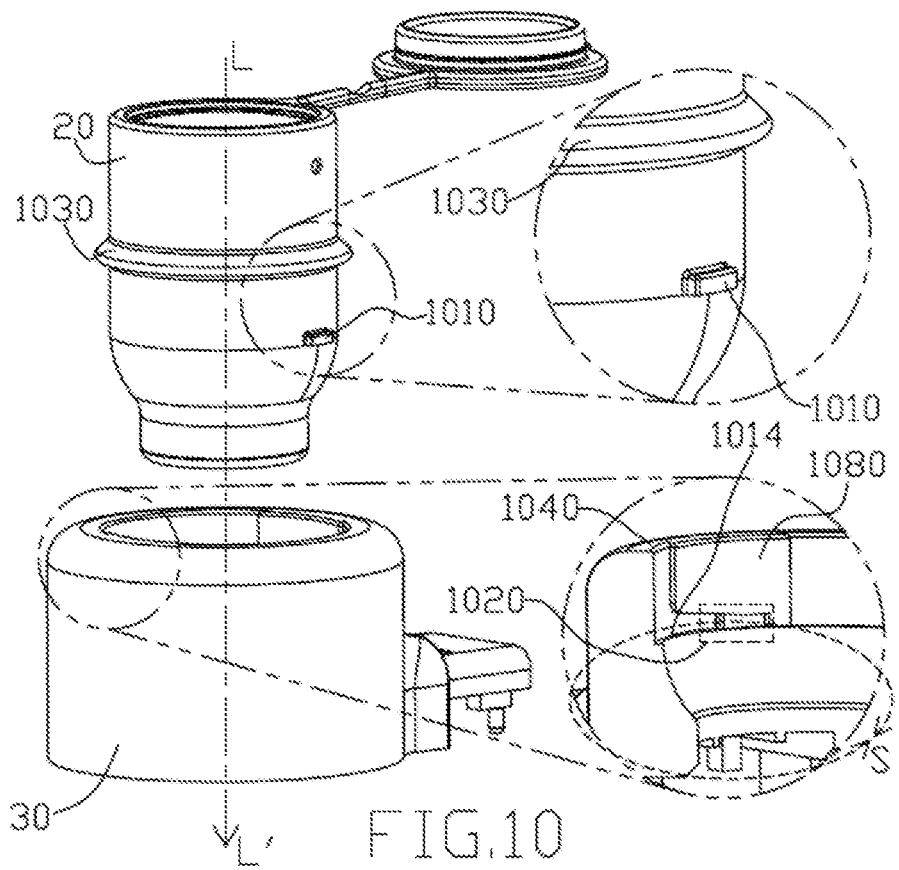
FIGS. 10-14 schematically illustrate an aerosol generating apparatus, in which a liquid container slidably and detachably mates and engages with an adaptor via respective mating elements according to some embodiments of the present disclosure.
Figure 11:
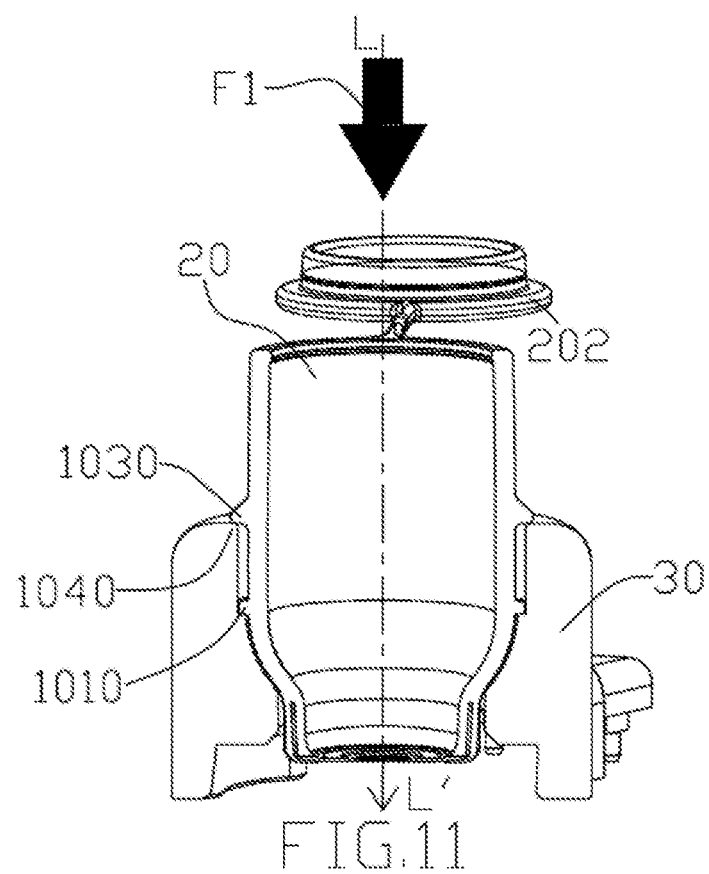
Figure 12:
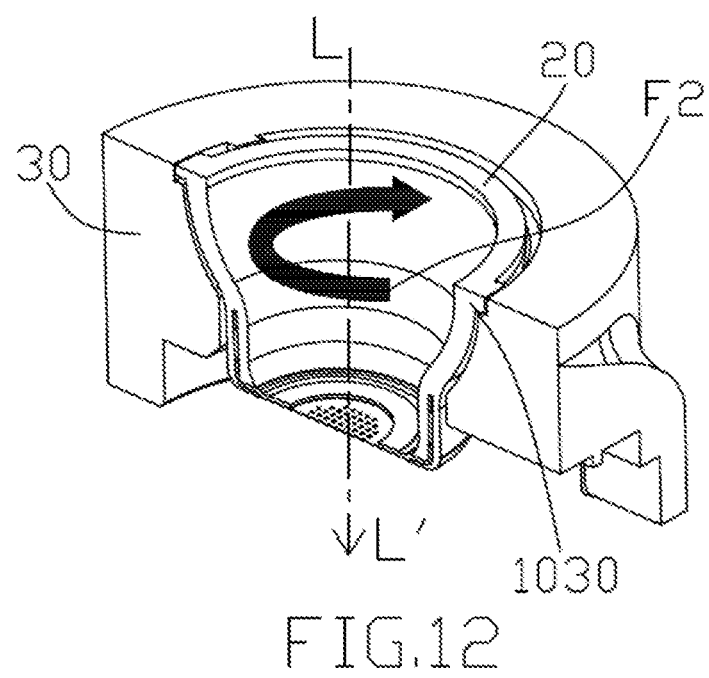
Figure 13:
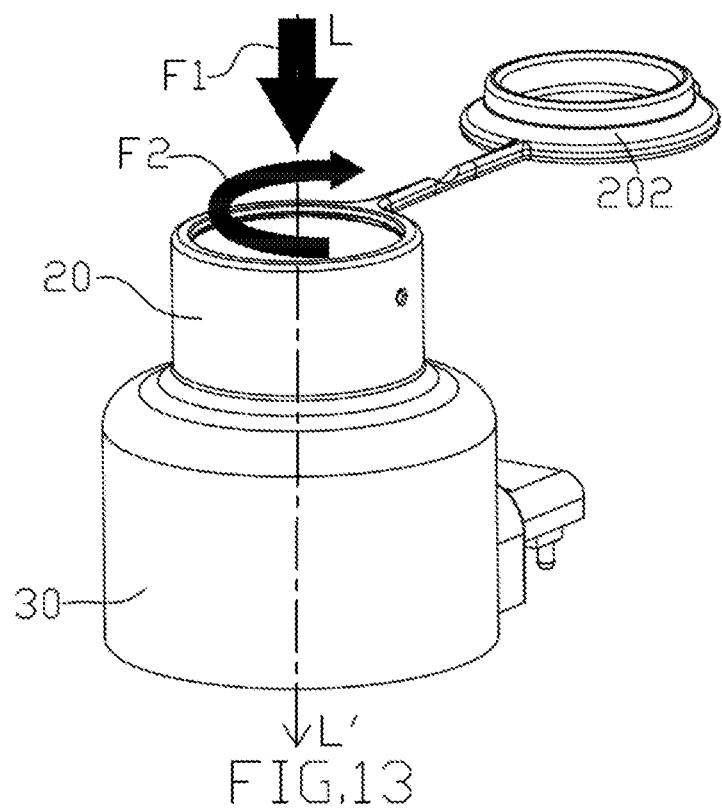
Figure 14:
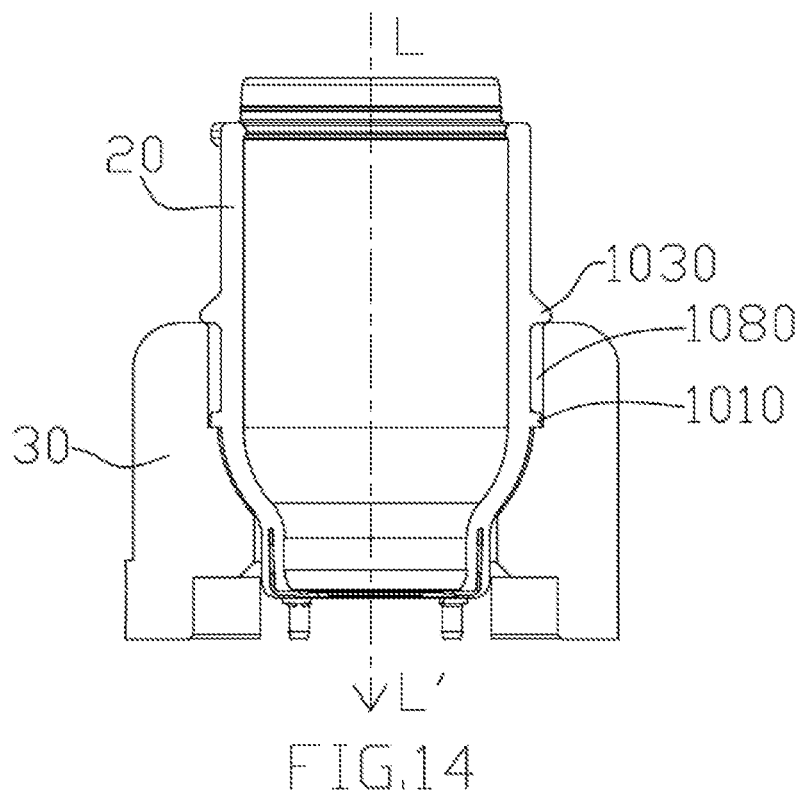

FIGS. 8-9 are partial and lateral views of an aerosol generating apparatus with interchangeable parts in accordance with some embodiments of the present disclosure.

FIG. 8 is a partial view of the aerosol generating apparatus 10 in the engaged state. The membrane 204 is in direct contact with but not pressed inward by the projection 408 extending from the face of the inlet surface 402 of the structure plate 40. Thus, the interface between the membrane 204 and the top surface of the projection 408 is substantially leveled. Alternatively, an additional layer, such as a protection layer or a coating, may be provided between the membrane 204 and the projection 408. Still, as long as neither the transmission of vibration energy from the projection 408 to the membrane 204 nor the detachability of the projection 408 and the membrane 204 is affected, any layer may be added between the projection and the membrane and the two should still be considered as in direct contact.

In some embodiments, the projection 408 includes a top surface facing the membrane 204 when engaged, and the section of such top surface in contact with the membrane 204 is the working surface 4082. In FIG. 8, the working surface 4082 is the same size as the top surface of the projection 408. The working surface 4082 serves as the interface for transmitting the vibration energy from an oscillation generator 50 to the membrane 204 for aerosolization. As shown in FIGS. 8-9, the dimension, i.e., area, of the working surface 4082 is subject to change. The factors affecting its dimension may include size of the projection or the membrane, shape of the working surface, shape of the projection, extent of the membrane being pushed inward by the projection, material of the membrane, and so on. The dimension of the working surface 4082 may also be adjusted according to the purpose of the aerosol generating apparatus or the liquid medicament contained therein. In a preferred embodiment, the dimension of the working surface 4082 is not larger than that of the membrane 204 to ensure desired aerosolization efficiency.

In some embodiments, when the membrane 204 is in contact with the projection 408, a space 410 is formed between the membrane 204 and the inlet surface 402. The space 410 is preserved because not the entire membrane 204 is in contact with the projection 408. As vibration energy is transmitted from the oscillation generator 50 to the membrane 204 through the working surface 4082, those sections of the membrane 204 not in touch with or affected by the projection 408 are in free-form. Here, being in "free-form" or "free-form movement" means that the vibration of the membrane 204 is not affected by undesirable influences of surrounding component(s) or structure(s) of the aerosol generating apparatus. In addition "free-form" or "free-form movement" means that the membrane 204 is capable of reaching a resonance state corresponding to the vibration energy received from the projection 408. Hence, although certain section of the membrane 204 is in contact with and influenced by the projection 408, the membrane 204 is in "free-form" or "free-form movement" as long as it's capable of resonating. The formation of the space 410 helps to preserve the free-form movement of the membrane 204. As such, aerosolization efficiency is improved because energy from the oscillation generator 50 is more effectively transmitted to the membrane 204 for vibration.

In certain embodiments, the structure plate 40 includes a planar part 412 at the inlet surface 402, and the planar part 412 extends annually from the projection 408. As depicted in FIG. 8, the space 410 substantially corresponds to the planar part 412. Accordingly, the planar part 412 is not in contact with the membrane 204 in the engaged state such that those parts of the membrane 204 corresponding to the planar part 412 is in free-form and the vibration thereof is not affected by the planar part 412 of the structure plate 40. In other words, the planar part 412 is neither sealed by the membrane 204, nor isolated from the interior environment of the aerosol generating apparatus 10 by the membrane 204 in the engaged state. Furthermore, the sidewall of the projection 408 is not isolated from the interior environment of the aerosol generating apparatus in the engaged state. The foregoing also ensures that the membrane 204 is capable of free-form movement in the engaged state.

FIG. 9 is a partial view of the aerosol generating apparatus 10 in an engaged state. Here, the projection 408 presses the membrane 204 inward for a distance D. The distance D is measured from the upper surface of the membrane 202 to its lowest point of indention. The distance D also represents the extent in which the membrane 204 is pressed by the projection 408. The distance D may correlate to at least a relative movement between the liquid container 20 and the adaptor 30. Detail of the correlation will be described later.

In some embodiments, a space 410' may be formed between the upper surface of the projection 408 and the membrane 204. As such, the dimension of the working surface 4082 of the projection 408 is reduced because its area of contact with the membrane 204 is reduced. Still, as long as there is some working surface 4082 and vibration energy can be transmitted from the projection 408 to the membrane 204, such configuration is within the scope of the present disclosure. In some embodiments, the distance D is less than the height H because not the entire projection 408 is pushed inward against the membrane 204. Thus, sections of the membrane 204 other than those in contact with the projection 408 are in free from and vibration of which is not affected by the projection 408 or the structure plate 40. In certain embodiments, the distance D can be adjusted pursuant to the need of the aerosol generating apparatus and the particle size of the liquid medicament.

In certain embodiments, the height H of the projection 408 is no less than 0.1 mm in order to preserve the space 410 and the free-form movement of those sections not in contact with the structure plate 40 and/or the projection 408. In other embodiments, the distance D is less than the height H to ensure that less than the entire projection 408 is pushed inward against membrane 204. The benefits of the foregoing arrangement have been discussed in preceding paragraph and will not be repeated.

The present disclosure also discloses a mechanism that adjusts the length of the distance D using specific features of the liquid container 20 and the adaptor 30.

FIGS. 10-14 schematically illustrate the liquid container 20 slidably and detachably mates and engages with the adaptor 30 via their respective mating elements according to some embodiments of the present disclosure. The liquid container 20 has a first mating element 1010. The adaptor 30 has a second mating element 1020 that can mate and engage with the first mating element 1010 in a mutually slidable and detachable manner. The second mating element may locate at either the body 302 or the interface 304.

In one embodiment, the first mating element 1010 may be a tongue. The second mating element 1020 may be a groove formed between a stopper 1080 and an inner edge 1014. When the liquid container 20 is to engage the adaptor 30, the first mating element 1010 is adapted to slidably move along a sliding axis S into the receiving second mating element 1020 via the inner edge 1014. When the first mating element 1010 abuts the stopper 1080, a full mate condition is reached. In other words, the two mating elements are engaged and the liquid container 20 and adaptor 30 are locked. Note that the sliding movement is not limited to the first mating element 1010. Inversely, the second mating element may slidably move in the opposite direction to engage the first mating element.

In another embodiment, there can be more than one first mating element on the liquid container 20. Reciprocally, there can be more than one second mating element in the adaptor 30 to mate and engage the more than one first mating element.

In another embodiment, a third mating element 1030 may annuarly extend around the liquid container 20 in the shape of a protruding ring. A fourth mating element 1040 may locate at the top edge of the adaptor 30 to mate and engage the third mating element 1030. For example, the fourth mating element 1040 may be a circular edge adapted to make contact with the protruding ring of the third mating element 1030 during mating operation, thereby preventing the third mating element (and the liquid container 20) from further downward movement. In other words, the third mating element is adapted to rest on the fourth mating element during engagement, allowing the vertical position of the liquid container 20 to maintain station. When the third and fourth mating elements are engaged, the first and second mating elements may slidably move to engage each other.

FIG. 10 shows the liquid container 20 and the adaptor 30 in a disengaged state.

In FIG. 11, a downward relative movement of the liquid container 20 along the dotted line from L to L' is initiated by a downward force Fl. The third mating element 1030 mates with the fourth mating element 1040 by contacting or resting on the fourth mating element, while the first mating element sits on the inner edge 1014. At this state, the projection 408 of the substrate 402 may be in contact with the perforated membrane 204. The downward force F1 may be initiated by a user or by any mechanical means.

FIG. 12 and FIG. 13 illustrate the manner in which the first mating element 1010 mates and engages the second mating element 1020. FIG. 12 shows the first mating element 1010, initially sitting on the inner edge 1014, slidably moves into the second mating element 1020 by a rotational force F2. This sliding movement serves to engage the two mating elements while also allow the aperture 406 to align proximately to the center of the perforated membrane 204. As noted above, the second mating elements may also slidably move to catch the first mating element by a rotational force opposite to F2. The present invention does not limit the sliding movement of the first and second mating elements as long as proper engagement can be achieved. FIG. 13 illustrates a full mate condition where all mating elements are properly engaged. Accordingly, the relative position of the liquid container 20 and adaptor 30 is fixed.

FIG. 14 illustrates the successful engagement of the liquid container 20 and adaptor 30 where the perforated membrane 204 and the aperture 406 are properly aligned and the projection 408 presses against the perforated membrane 204.

The extent in which the projection 408 presses the membrane 204, e.g. the distance D shown in FIGS. 8 and 9, can be adjusted based on the position of the first and second mating elements 1010 and 1020 and/or the third and fourth mating elements 1030 and 1040, relative to the liquid container 20 and adaptor 30. For example, lowering the positions of the mating elements 1010 and 1020 will cause the projection 408 to press more against the perforated membrane 204, i.e., increasing the distance D. Conversely, raising the positions of the mating elements 1010 and 1020 will cause the projection 408 to press less against the perforated membrane 204, i.e., decreasing the distance D.

Figure 15:
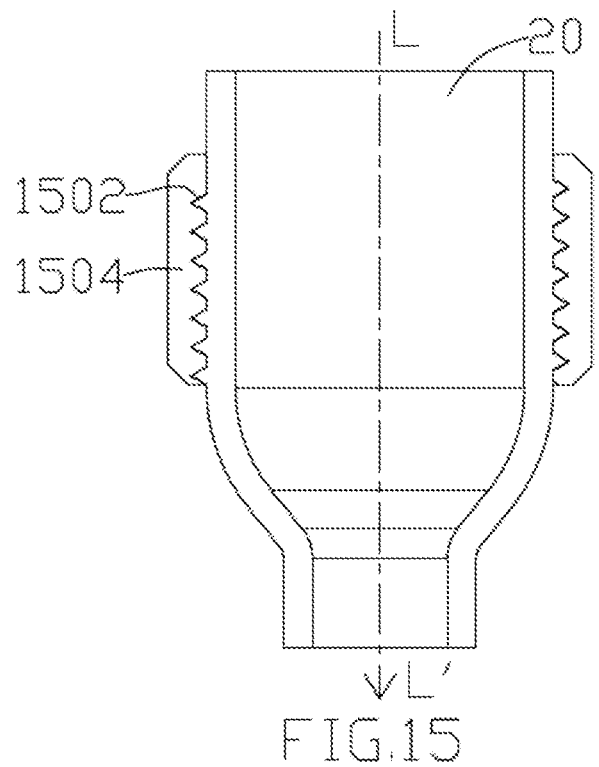
FIGS. 15-20 illustrate an aerosol generating apparatus that utilizes other types of connection in which a first mating element and a second mating element can be engaged.
Figure 16:
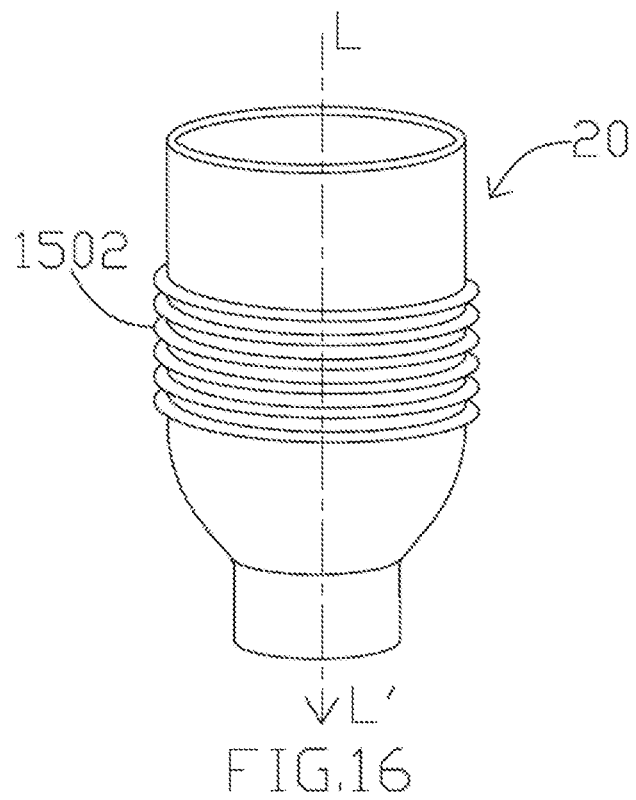

FIGS. 15-20 illustrate other types of connection in which the first mating element 1010 and the second mating element 1020 can be engaged. As shown in FIGS. 15 and 16, the first mating element 1010 includes a helical threaded surface 1502 and the second mating element 1020 includes a helical threaded surface 1504. The helical threaded surface 1502 mates with the helical thread surface 1504 while the liquid container 20 rotates down along the direction of dotted line from L to L'. When the liquid container 20 can no longer be rotated, either because the end of helical thread or a stopper is reached, a full mate condition is achieved and the liquid container 20 is affixed with the adaptor 30.

Figure 17:
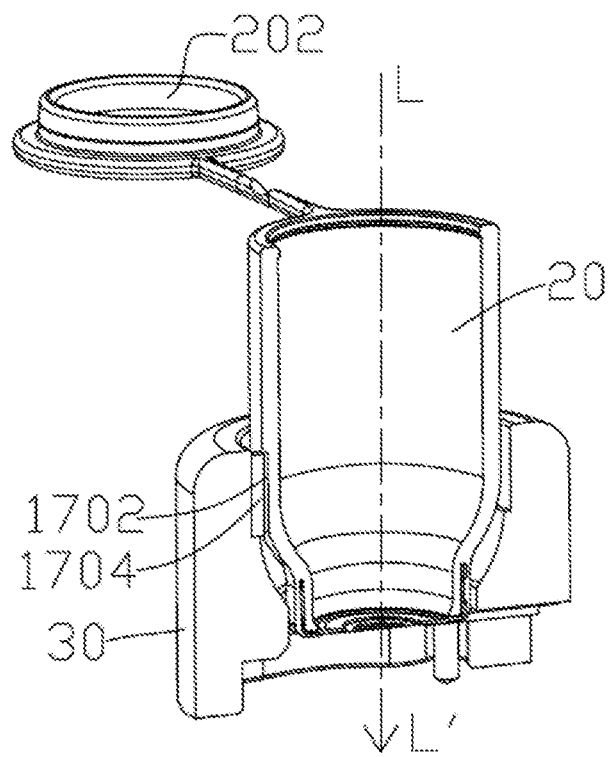
Figure 18:
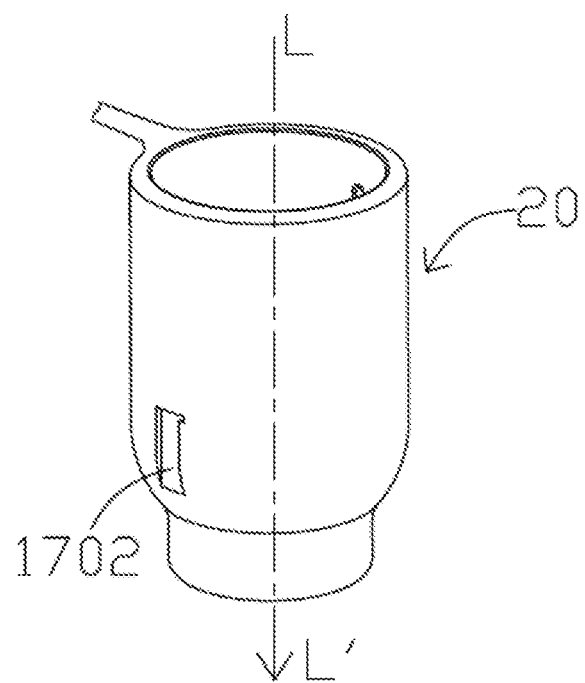

In some examples of the present disclosure, as shown in FIGS. 17 and 18, the first mating element 1010 includes a groove 1702 and the second mating element 1020 includes a tongue 1704. The groove 1702 slidably mates with the tongue 1704 in a similar manner as described above. When the tongue 1704 is properly received in the mating groove 1702, a full mate condition is reached.

Figure 19:
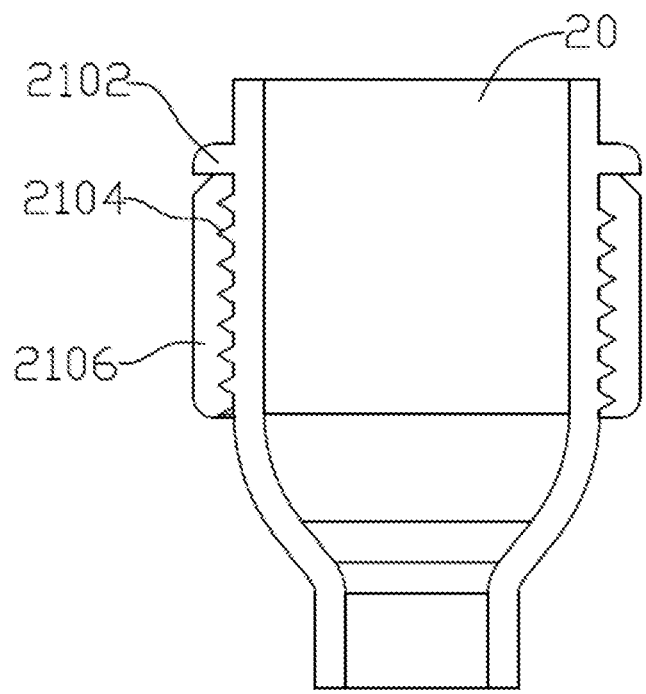
Figure 20:
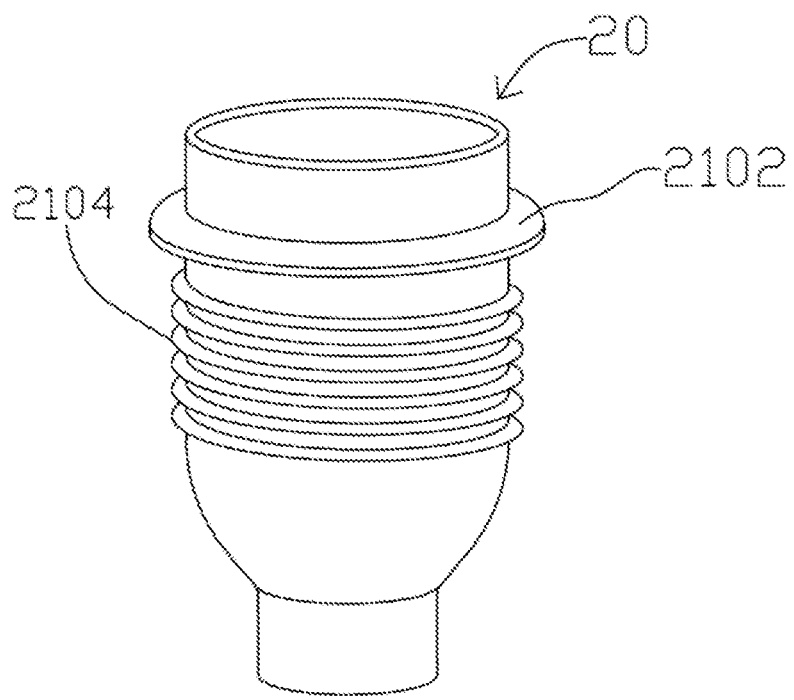

In some examples of the present disclosure, as shown in FIGS. 19 and 20, the first mating element 1010 includes a stopper 2102 and a helical threaded surface 2104, and the second mating element 1020 includes a helical threaded surface 2106. As the liquid container 20 rotates down along the helical thread in the direction of L to L', the helical threaded surface 2104 mates with the helical threaded surface 2106. When the stopper 2102 makes contact with the upper edge of the second mating element 1020, it stops the liquid container 20 from rotating down further. A full mate condition is reached and the position of the liquid container 20 and adaptor 30 is fixed.

Figure 21:
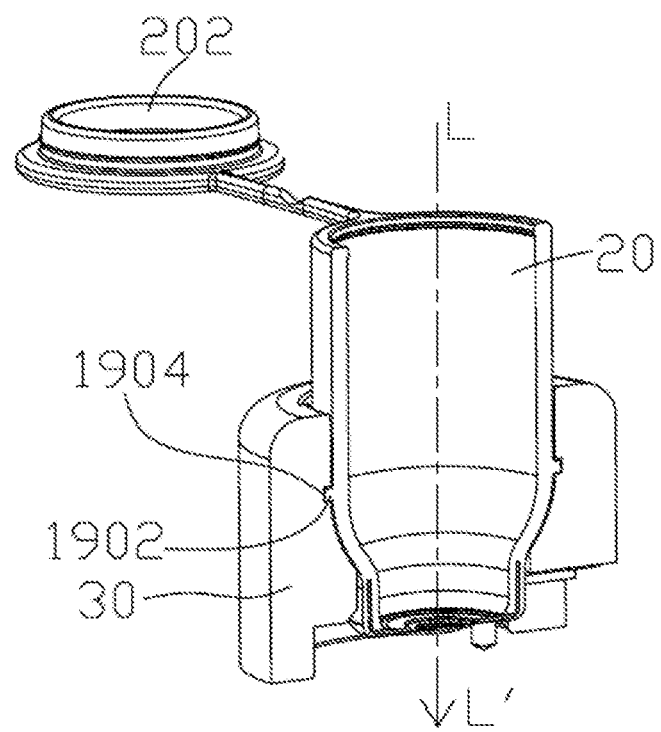
FIGS. 21-32 illustrate an aerosol generating apparatus that utilizes connection mechanisms that do not involve sliding or rotating movements according to some embodiments of the present disclosure.
Figure 22:
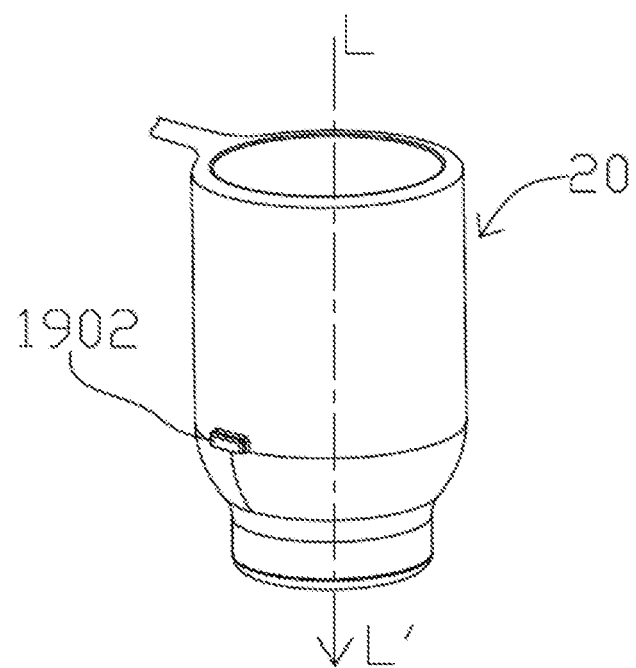

In FIGS. 10-20, the connection mechanisms described involve either a sliding or a rotational movement. However, connection mechanisms that do not involve sliding or rotating movements are also applicable in the present invention, as illustrated in FIGS. 21 and 22. In some examples of the present disclosure, the mating elements can mate and engage using a connection such as a snap fit, an interference fit, a (non-sliding) tongue-and-groove fit, a post-and-bore fit, or a press fit.

In FIGS. 21 and 22, the first mating element 1010 includes a protruding part 1902 and the second mating element 1020 includes a cavity 1904. The protruding part 1902 can be a hook, stud or bead. When the liquid container 20 moves downwardly into the adaptor 30 in the direction of L to L', the protruding part 1902 is deflected briefly during the joining operation and catches in the mating cavity 1904 of the adaptor 30. After engagement, this snap-fit features should return to a stress-free condition. The engagement may be separable or inseparable depending on the shape of the cavity 1904.

Under the snap-fit connection, the extent in which the projection 408 presses against the membrane 204 may correspond to a relative movement of the first mating element 1010 (i.e., the protruding part 1902) in the longitudinal direction, i.e., along the dotted line from L to L'. In other words, distance D may correlate to how far the first mating element can move downward in respective to the adaptor 30.

FIGS. 23-32 disclose other examples of the present disclosure that apply connection mechanisms similar to the one shown in FIGS. 21-22.

Figure 23:
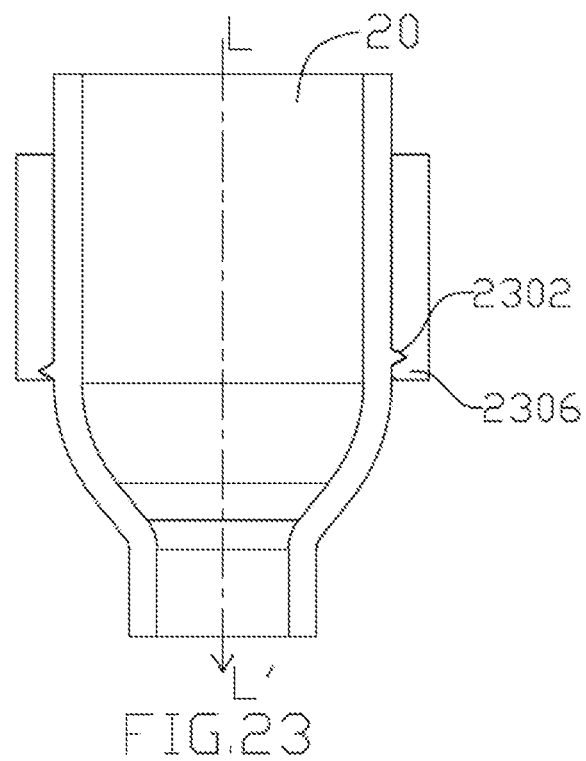
Figure 24:
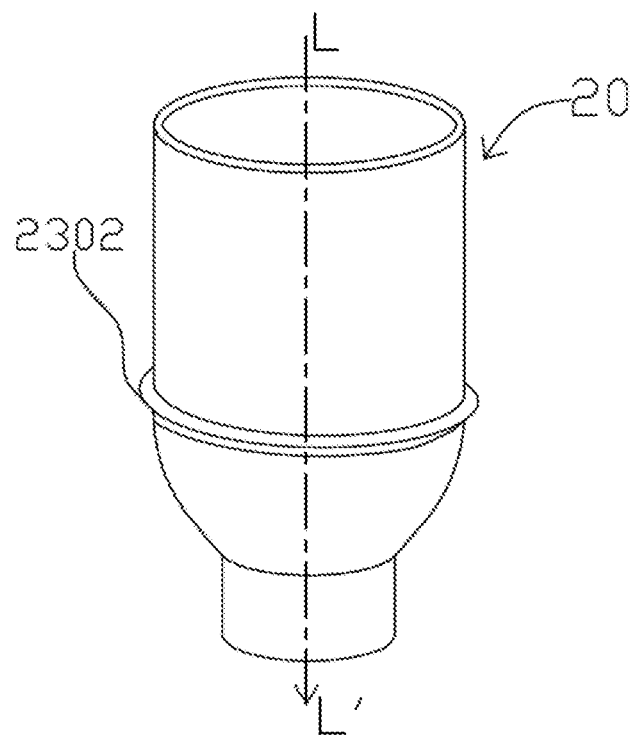

In FIGS. 23 and 24, the first mating element 1010 includes a protruding part 2302 that extends annuarly around the liquid container 20, and the second mating element 1020 includes a cavity 2306. When the liquid container 20 moves in the direction from L to L', the protruding part 2302 mates and engages the cavity 2306 via an interference or press fit.

Figure 25:
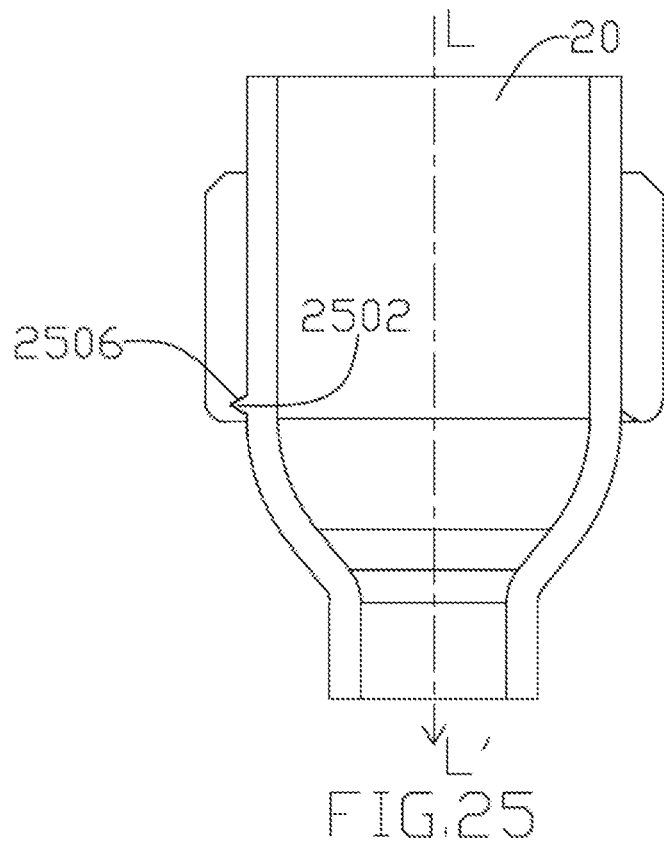
Figure 26:
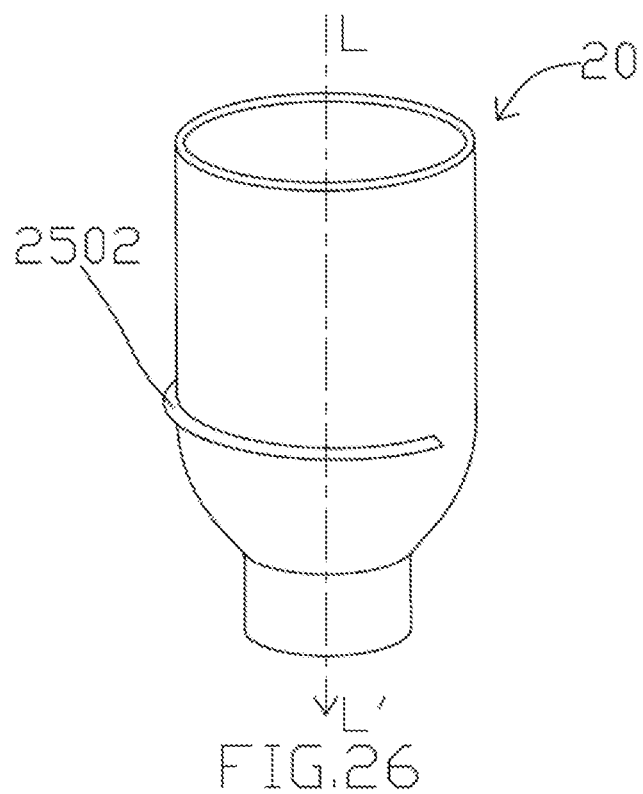

In FIGS. 25 and 26, the first mating element 1010 includes a protruding part 2502 that extend semi-annuarly around the liquid container 20, and the second mating element 1020 includes a mating cavity 2506. The two mating elements can be connected using an interference fit or press fit.

Figure 27:
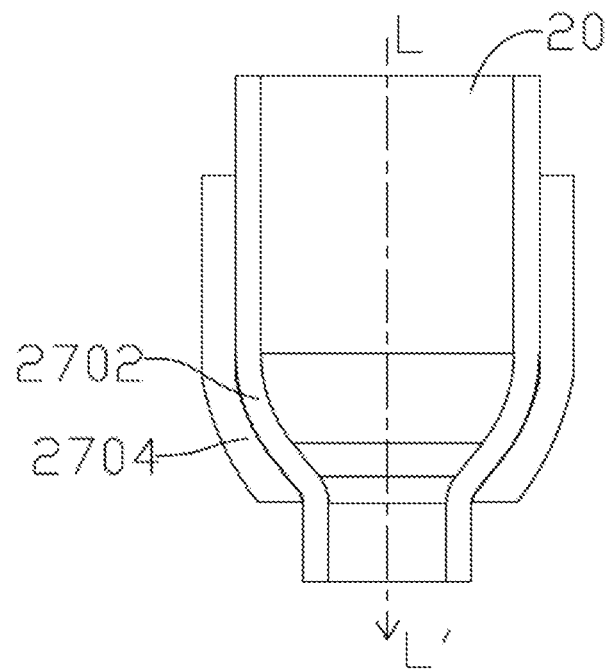
Figure 28:
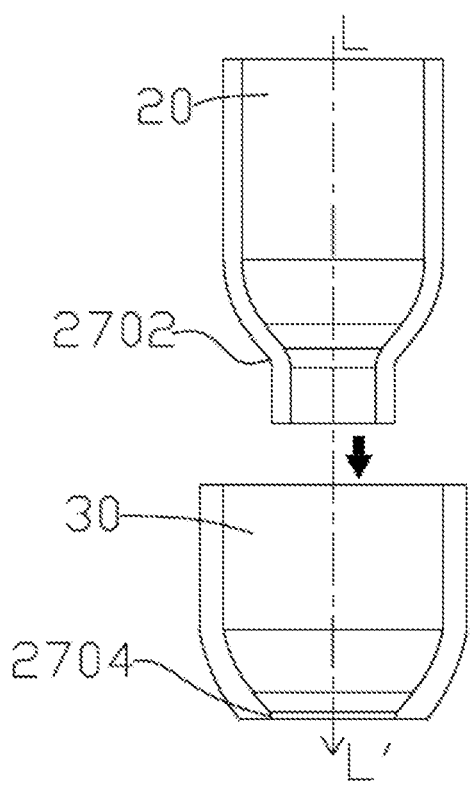

In FIGS. 27 and 28, the first mating element 1010 includes a contact surface 2702, and the second mating element 1020 includes a contact surface 2704. The contact surfaces 2702 and 2704 are adapted in a manner such that friction occurs between the two contact surfaces to create a friction or press-fit.

Figure 29:
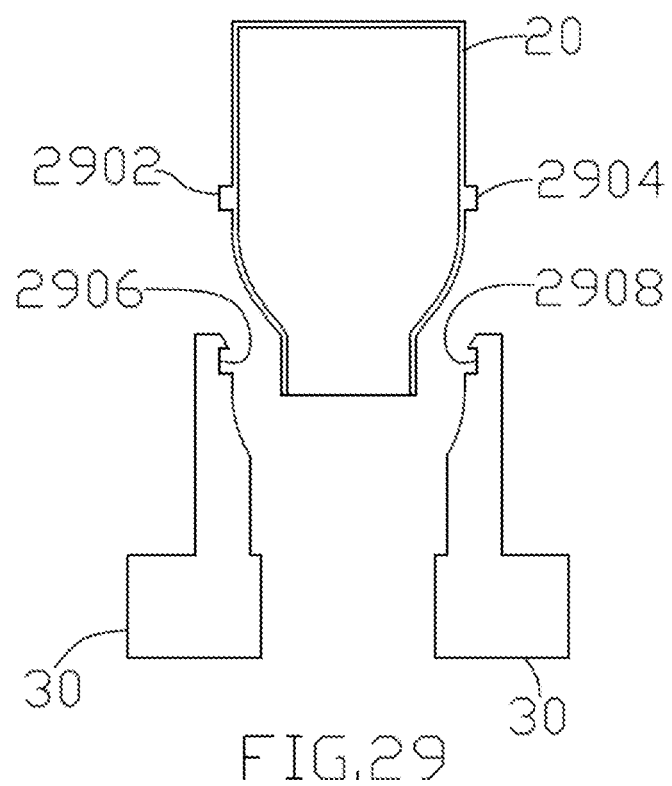
Figure 30:
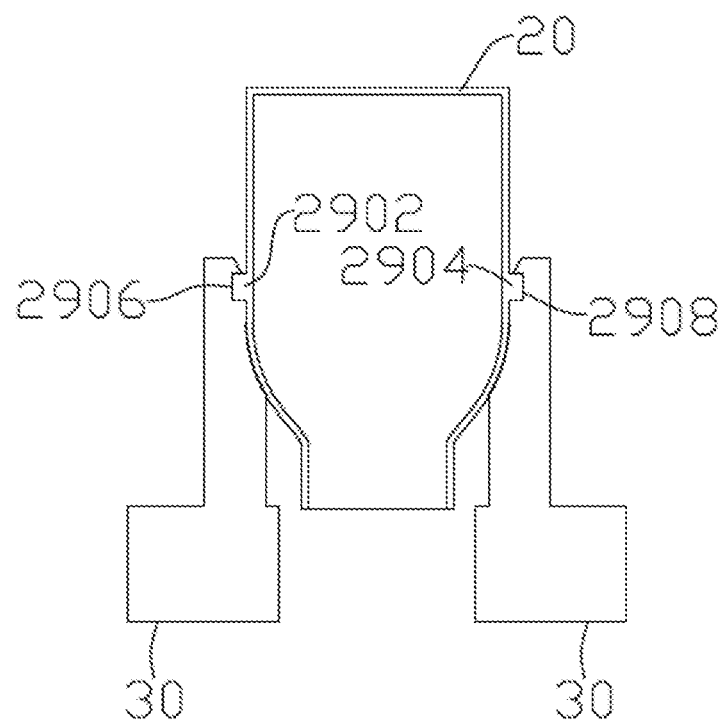

In FIGS. 29 and 30, the first mating element 1010 includes two protruding parts 2902 and 2904, and the second mating element 1020 includes two mating cavities 2906 and 2908. The two mating elements can be joined via a snap-fit configuration.

Figure 31:
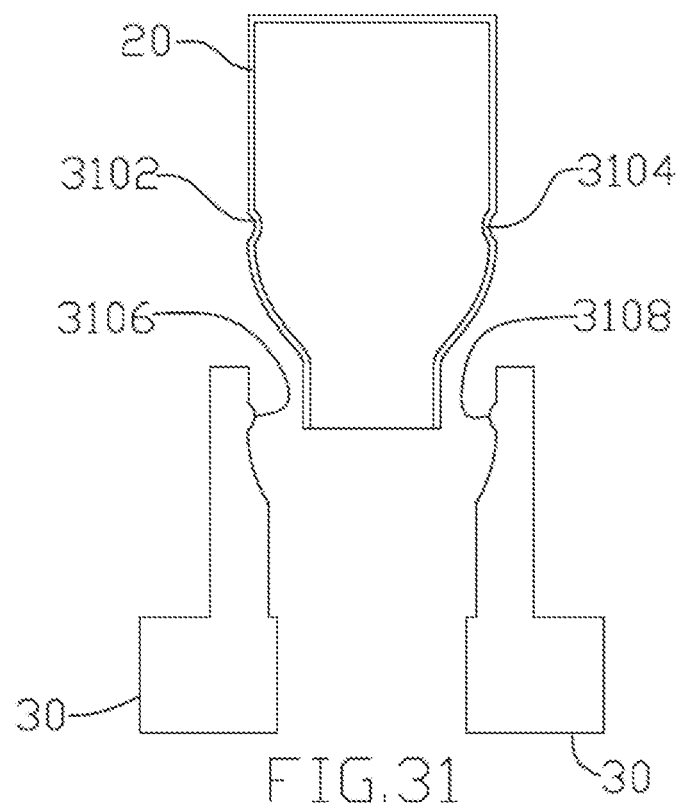
Figure 32:
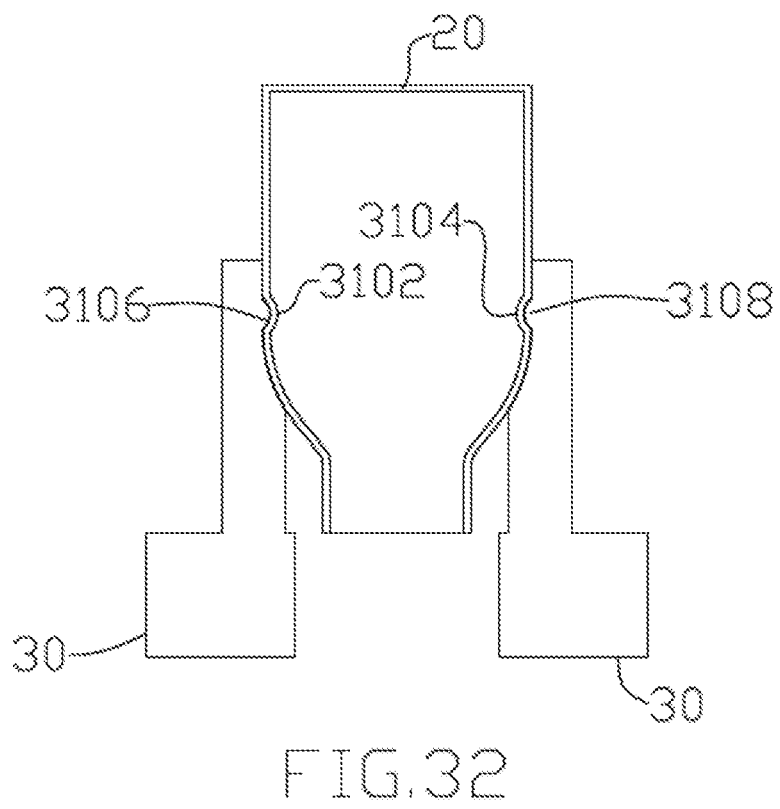

In FIGS. 31 and 32, the first mating element 1010 includes two cavities 3102 and 3104, and the second mating element 1020 includes two mating protruding parts 3106 and 3108. The two mating elements can be joined via a snap-fit configuration.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

LISTING OF ELEMENTS aerosol generating apparatus 10
liquid container 20
lid 202
membrane 204
orifice 206 adaptor 30
body 302
interface 304
through hole 306
jack 308
driving element 40
substrate 402
PZT element 404
aperture 406
projection 408
working surface 4082
mating structure 410
electric contact 412
aerosol 50
space S1
first mating element 1010
inner edge 1014
second mating element 1020
third mating element 1030
fourth mating element 1040
stopper 1080, 2102
helical threaded surface 1502, 1504, 2104, 2106
groove 1702
tongue 1704
protruding part 1902, 2302, 2502, 2902, 2904
cavity 1904, 2306, 2506, 3102, 3104
contact surface 2702, 2704
mating cavity 2906, 2908
mating protruding part 3106, 3108

What is claimed is:

1. An aerosol generating apparatus, comprising:
   a dosage liquid container having a first end and a second end, an opening at the second end, and a perforated membrane covering the opening defining a membrane surface through which liquid can permeate;
   an adaptor configured to releasably couple with the second end of the container, the adaptor including a receiving portion, wherein the receiving portion includes at least one jack;
   a driving element including a substrate adjacent a piezoelectric element, wherein the substrate includes an aperture and a projection, and wherein at least a portion of the driving element is configured to be supported by the at least one jack of the receiving portion of the adaptor, and wherein the substrate includes at least one corresponding mating structure to mate with the structure of the at least one jack; and
   an attachment assembly configured for coupling the container and the adaptor, the attachment assembly including a first attachment element on the container configured to be attached with a second attachment element on the adaptor, such that when the first and second attachment elements are attached, a portion of the driving element presses against the membrane surface such that the aperture of the substrate aligns with the membrane surface and the projection of the substrate presses against the membrane surface, and at least a portion of the driving element is supported by the receiving portion of the adaptor, and such that when the first and second attachment elements are detached, the container is detached from the adaptor and the driving element is released from pressing against the membrane surface of the container.

2. The aerosol generating apparatus of claim 1, wherein the at least one jack is part of a jack system disposed in the receiving portion of the adaptor for contacting and supporting the driving element.

3. The aerosol generating apparatus of claim 2, wherein the jack system includes at least two or three jacks.

4. The aerosol generating apparatus of claim 2, wherein the jack system is configured to support only a portion of an outer perimeter of the substrate.

5. The aerosol generating apparatus of claim 1, wherein the first and second attachment elements are configured to attach to each other using a connection selecting from the group consisting of a snap-fit, an interference fit, a tongue-and-groove fit, a post-and-bore fit, and a press-fit.

6. The aerosol generating apparatus of claim 1, wherein a degree to which the projection presses against the membrane surface is predetermined by the positions of the first and second attachment elements.

7. The aerosol generating apparatus of claim 1, wherein the first attachment element is configured to move in a longitudinal direction.

8. The aerosol generating apparatus of claim 7, wherein the degree to which the projection presses against the membrane surface correlates to a relative movement of the first attachment element in the longitudinal direction.

9. The aerosol generating apparatus of claim 1, wherein the first and second attachment elements are configured to move along a sliding axis until a full attachment condition is reached.

10. The aerosol generating apparatus of claim 1, wherein the first attachment element includes a groove or a tongue which engages a tongue or a groove on the second attachment element.

11. The aerosol generating apparatus of claim 1, wherein the first attachment element includes a first helical thread surface which rotatably engages a second helical thread surface on the second attachment element.

12. The aerosol generating apparatus of claim 1, wherein the first attachment element includes a first contacting surface and the second attachment element includes a second contacting surface, the first and second contacting surfaces are adapted to create friction such that the liquid container and the adaptor are securely engaged.

13. The aerosol generating apparatus of claim 1, wherein the first attachment element includes a protruding part and the second attachment element includes a cavity wherein the protruding part is configured for temporary deflection during attachment before resting in the cavity.

14. The aerosol generating apparatus of claim 13, wherein the protruding part is selected from a group consisting of a hook, a stud, or a bead.

15. The aerosol generating apparatus of claim 13, wherein the protruding part extends annularly or semi-annularly around the container and the cavity extends annularly or semi-annularly inside the adaptor.

16. The aerosol generating apparatus of claim 1, wherein the dosage liquid container includes a third attachment element configured to annularly surround the dosage liquid container and the adaptor includes a fourth attachment element configured to locate at a top edge of the adaptor, wherein the third and fourth attachment elements are adapted to attach and engage with each other such that the vertical position of the dosage liquid container maintains stationary.

17. The aerosol generating apparatus of claim 1, wherein the at least one corresponding mating area of the substrate defines at least one indentation or recess corresponding to the at least one jack.

18. A method of using an aerosol generating apparatus, comprising:

obtaining a dosage liquid container having a first end and a second end, an opening at the second end, and a perforated membrane covering the opening defining a membrane surface through which liquid can permeate;

obtaining an adaptor configured to releasably couple with the second end of the container, the adaptor including a receiving portion, wherein the receiving portion includes at least one jack;

obtaining a driving element including a substrate adjacent a piezoelectric element, wherein the substrate includes an aperture and a projection and wherein the substrate includes at least one corresponding mating structure to mate with the structure of the at least one jack;

attaching the dosage liquid container to the adaptor using an attachment assembly including a first attachment element on the container configured to be attached with a second attachment element on the adaptor, such that when the first and second attachment elements are attached, a portion of the driving element presses against the membrane surface such that the aperture of the substrate aligns with the membrane surface and the projection of the substrate presses against the membrane surface, and at least a portion of the driving element is supported by the receiving portion of the adaptor; and detaching the container from the adaptor such that when the first and second attachment elements are detached, the driving element is released from pressing against the membrane surface of the container.

19. An aerosol generating apparatus, comprising:

a dosage liquid container having a first end and a second end, an opening at the second end, and a perforated membrane covering the opening defining a membrane surface through which liquid can permeate;

an adaptor configured to releasably couple with the second end of the container, the adaptor including a receiving portion and a jack system disposed in the receiving portion of the adaptor;

a driving element including a substrate adjacent a piezoelectric element, wherein the substrate includes an aperture and a projection, and wherein at least a portion of the driving element is configured to be supported by the jack system disposed in the receiving portion of the adaptor and wherein the substrate includes a corresponding mating structure to mate with the structure of the jack system; and an attachment assembly configured for coupling the container and the adaptor, the attachment assembly including a first attachment element on the container configured to be attached with a second attachment element on the adaptor, such that when the first and second attachment elements are attached, a portion of the driving element presses against the membrane surface such that the aperture of the substrate aligns with the membrane surface and the projection of the substrate presses against the membrane surface, and at least a portion of the driving element is supported by the jack system disposed in the receiving portion of the adaptor, and such that when the first and second attachment elements are detached, the container is detached from the adaptor and the driving element is released from pressing against the membrane surface of the container.

* * * * *